United States Patent [19]

Gosteli

[11] 4,138,451

[45] Feb. 6, 1979

[54] PHOSPHONO-ISOCYANO-ACETATES

[75] Inventor: Jacques Gosteli, Basel, Switzerland

[73] Assignee: Ciba-Geigy Corporation, Ardsley, N.Y.

[21] Appl. No.: 791,757

[22] Filed: Apr. 28, 1977

Related U.S. Application Data

[62] Division of Ser. No. 608,798, Aug. 28, 1975, Pat. No. 4,045,520.

[30] Foreign Application Priority Data

Sep. 11, 1974 [CH] Switzerland ............... 12353/74

[51] Int. Cl.$^2$ ............................................. C07F 9/40
[52] U.S. Cl. ............................ 260/940; 260/327 TH; 260/332.2 R; 260/345.8 R; 260/347.4
[58] Field of Search ............. 260/940, 345.8, 347.4, 260/327 TH, 332.2 R

[56] References Cited

U.S. PATENT DOCUMENTS 3,286,000  11/1966  Ugi et al. ............... 260/940

*Primary Examiner*—Anton H. Sutto
*Attorney, Agent, or Firm*—John J. Maitner

[57] ABSTRACT

Thioformamidophosphono-acetates are prepared by reacting an isocyano compound of the formula $C{=}N{-}CH_2{-}X_1$ in the presence of a base with a compound of the formula $R_o{-}X_2$, in which compounds one of the groups $X_1$ and $X_2$ represents a protected carboxyl group of the formula $-C({=}O){-}OR_1$ and the other a disubstituted phosphono group of the formula $-P({\to}O)(OR)_2$, and wherein $R_o$ represents a reactive etherified or esterified hydroxyl group, and adding hydrogen sulphide on to the isocyano group of the phosphono-isocyano-acetate formed as an intermediate.

3 Claims, No Drawings

PHOSPHONO-ISOCYANO-ACETATES

This is a division of application Ser. No. 608,798, filed Aug. 28, 1975 now U.S. Pat. No. 4,045,520. The invention relates to a new process for the manufacture of thioformamido-phosphono-acetates of the formula

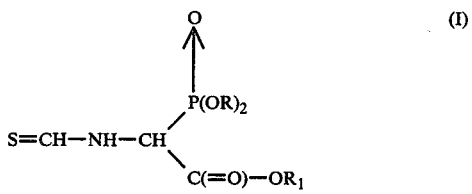

wherein R represents lower alkyl, aryl or aryl-lower alkyl and $R_1$ represents a radical which protects the carboxyl group, as well as new intermediate products which are used in the process according to the invention.

In the compounds of the present invention the two radicals R can be identical or different. One radical R is preferably lower alkyl with 1–7, preferably 1–4, carbon atoms, such as methyl, propyl, butyl, pentyl, hexyl, heptyl or especially ethyl; aryl, preferably with up to 18 carbon atoms, such as optionally substituted phenyl, such as halogenophenyl, lower alkoxyphenyl or lower alkylphenyl, for example phenyl, p-chlorophenyl, p-methoxyphenyl or p-methylphenyl; or aryllower alkyl, preferably with up to 18 carbon atoms, especially benzyl.

A radical $R_1$ which protects the carboxyl group is preferably an optionally substituted organic radical with preferably up to about 20 carbon atoms. Such organic radicals are, for example, aliphatic, cycloaliphatic, cycloaliphatic-aliphatic, aromatic or araliphatic radicals, especially optionally substituted hydrocarbon radicals of this type.

In the compounds of the present invention $R_1$ is preferably one of the carboxyl protective groups which are customary in cephalosporin chemistry for protecting the carboxyl group in the 4-position of the cepham ring system and is preferably easily removable and enables the protected carboxyl group to be converted readily into a free carboxyl group or into another functionally modified carboxyl group, such as into a carbamoyl or hydrazinocarbonyl group.

Suitable radicals $R_1$ are, for example, optionally substituted alkyl or aralkyl radicals with 1 to 20 carbon atoms.

Preferred radicals $R_1$ are lower alkyl radicals with 1 to 7, preferably 1 to 4, carbon atoms, such as methyl, ethyl, n-propyl or isopropyl, and especially tert.-lower alkyl groups, such as tert.-butyl or tert.-pentyl; substituted lower alkyl radicals, such as halogeno-lower alkyl, wherein halogen preferably has an atomic weight of more than 19, for example 2,2,2-trichloroethyl, 2-iodoethyl, 2-chloroethyl or 2-bromoethyl, lower alkoxy-lower alkyl or lower alkylthio-lower alkyl, such as methoxymethyl or methylthiomethyl or 2-methoxyethyl or 2-methylthioethyl, aryloxy-lower alkyl, such as mono- or bis-(p-methoxyphenoxy)-methyl, or aralkoxy-lower alkyl, such as benzyloxymethyl; arylcarbonylmethyl, wherein aryl represents, in particular, an optionally substituted phenyl group, for example phenacyl or substituted phenacyl, for example p-bromophenacyl, polysubstituted methyl, which in a polycycloaliphatic hydrocarbon radical denotes a ring member or in an oxa-cycloaliphatic or thia-cycloaliphatic radical denotes the ring member which represents the α-position to the oxygen or sulphur atom, for example adamantyl, such as 1-adamantyl, 2-oxa- or 2-thia-cycloalkyl or -cycloalkenyl with 5–7 ring atoms, such as 2-tetrahydrofuryl, 2-tetrahydropyranyl or 2,3-dihydro-2-pyranyl or corresponding sulphur analogues; or aralkyl radicals with 1 or 2 aryl radicals, such as arylmethyl, wherein aryl denotes, in particular, a monocyclic optionally substituted aromatic hydrocarbon radical, such as lower alkyl-, lower alkoxy-, nitro- or halogeno-benzyl, for example 2,4,6-trimethylbenzyl, 3-, 4- and/or 5-methoxybenzyl or dimethoxybenzyl, 2- or 4-nitrobenzyl or 4,5-dimethoxy-2-nitrobenzyl, or diarylmethyl, such as optionally substituted diphenylmethyl, for example diphenylmethyl or 4,4'-dimethoxy-diphenylmethyl, as well as 2-(4-biphenylyl)-2-propyl.

Particularly preferred groups $R_1$ are lower alkyl groups with up to 4 carbon atoms, such as methyl or especially tert.-butyl, phenacyl, p-bromophenacyl, p-nitrobenzyl, 2,2,2-trichloroethyl, p-methoxybenzyl, diphenylmethyl, methoxymethyl and mono- and bis-(p-methoxyphenoxy)-methyl.

Compounds of the formula I in which R represents an alkyl or aryl group and $R_1$ represents a carboxyl protective group are already known from Netherlands Patent Application No. 73/04755 (see also R. W. Ratcliffe et al., Tetrahedron Letters 1973 (46), page 4,645–4,652). Hitherto, it has been possible to manufacture these compounds, which are valuable intermediate products in the total synthesis of cephalosporin compounds which have an antibiotic action, only by a tedious synthesis route which extends over several reaction stages.

According to the present invention it is possible, starting from known isocyano compounds or from isocyano compounds which can be produced in a manner which is in itself known, to manufacture compounds of the formula I in high yield and high purity in a surprisingly simple and advantageous manner in only two reaction stages.

The process according to the invention for the manufacture of compounds of the formula I is characterised in that an isocyano compound of the formula $C{\equiv}N{-}CH_2{-}X_1$ (II) is reacted in the presence of a base with a compound of the formula $R_o{-}X_2$ (III), one of the radicals $X_1$ and $X_2$ representing a group of the formula $-C(=O)-OR_1$ (A) and the other representing a group of the formula $-P(\rightarrow O)(OR)_2$ (B) and $R_o$ representing a reactive etherified or esterified hydroxyl group, and hydrogen sulphide is added on to the isocyano group of a resulting phosphono-isocyano-acetate of the formula

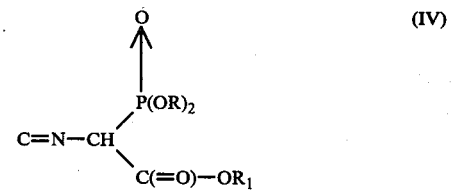

optionally after isolation thereof.

Suitable reactive compounds of the formula III are, on the one hand, phosphorylating phosphoric acid di-R ester derivatives of the formula III, wherein $X_2$ represents a group of the formula $-P(\rightarrow O)(OR)_2$ and $R_o$ for example preferably represents halogen, such as bromine, iodine or especially chlorine, or an esterified hydroxyl group, for example of the formula $(RO)_2(O\leftarrow)$-P—O—, wherein R has the same meaning as in the formula A, and, on the other hand, acylating carbonic acid monoester derivatives of the formula III, wherein $X_2$ denotes a group of the formula $-C(=O)-OR_1$ and $R_o$ for example preferably denotes halogen, such as bromine, iodine or especially chlorine, or an etherified hydroxyl group, such as, in particular, a radical which, together with the adjacent carbonyl grouping, forms an activated ester group. An etherified hydroxyl group $R_o$ in a carbonic acid monoester of the formula III is, for example, substituted phenoxy, such as nitrophenoxy, for example 4-nitrophenoxy, or 2,4-dinitrophenoxy, or polyhalogenophenoxy, such as 2,4,6-trichlorophenoxy or 2,3,4,5,6-pentachlorophenoxy.

Suitable bases for the phosphorylation of acylation reaction are those which are able to convert an isocyano compound of the formula II into the corresponding anion by removing an α-proton. Such bases are, for example, alkali metal hydrides, alkyls, aryls, amides or amines, such as sodium hydride, butyllithium, phenyl-lithium, sodium amide or lithiumdiisopropylamine.

The phosphorylation or acylation reaction is carried out, with exclusion of solvents containing hydroxyl groups, in an aprotic inert solvent, with cooling, at room temperature or with warming, for example at temperatures between about −50° C. and the boiling point of the solvent used, preferably at about −10° C. to room temperature. Suitable inert solvents are, for example, aliphatic, cycloaliphatic or aromatic, optionally substituted, such as halogenated, for example fluorinated or chlorinated, hydrocarbons, such as hexane, cyclohexane, benzene, toluene, xylene, methylene chloride, chloroform or carbon tetrachloride, ether-like solvents, such as di-lower alkyl ethers, for example diethyl ether or diisopropyl ether, 1,2-dimethoxyethane, tetrahydrofurane or dioxane, di-lower alkylamides, such as N,N-dimethylformamide or N,N-dimethylacetamide, lower alkyl cyanides, such as acetonitrile, di-lower alkyl sulphides, such as dimethyl sulphide, di-lower alkylsulphoxides, such as dimethylsulphoxide, or mixtures thereof.

Preferably, the basic agent is first allowed to react with the compound of the formula II, it being advantageous, if an alkali metal amide or amine is used, initially to remove the ammonia gas or amine which forms from the reaction solution, for example in vacuo, after which the reactive phosphoric acid di-R ester derivative or the reactive carbonic acid monoester derivative of the formula III is added to the reaction mixture and the condensation is carried on to completion.

Starting materials of the formula II and III are known or can be manufactured according to methods which are in themselves known.

The resulting intermediate product of the formula IV does not need to be isolated but can be subjected direct, in the original reaction solution, if necessary after filtering off insoluble by-products, such as sodium chloride or lithium chloride, to the addition reaction with hydrogen sulphide. However, the intermediate product can also be isolated in the customary manner and purified, for example chromatographically.

The addition reaction with hydrogen sulphide is carried out in an aprotic inert solvent, preferably in the presence of a suitable catalyst, with cooling, at room temperature about −10° C. and the boiling point of the solvent used, preferably at about 0° C. to room temperature. Suitable inert solvents are those used in the first reaction stage, for example aliphatic, cycloaliphatic or aromatic, optionally substituted, such as halogenated, for example fluorinated or chlorinated, hydrocarbons, such as hexane, cyclohexane, benzene, toluene, xylene, methylene chloride, chloroform or carbon tetrachloride, ether-like solvents, such as di-lower alkyl ethers, for example diethyl ether or diisopropyl ether, 1,2-dimethoxyethane, tetrahydrofurane or dioxane, di-lower alkylamides, such as N,N-dimethylformamide or N,N-dimethylacetamide, lower alkyl cyanides, such as acetonitrile, di-lower alkyl sulphides, such as dimethyl sulphide, di-lower alkylsulphoxides, such as dimethylsulphoxide, or mixtures thereof.

Suitable catalysts are the ions of monovalent or divalent heavy metals, such as zinc, cadmium, mercury and, especially, copper. The metal ions can be introduced into the reaction in the form of oxides, as salts of mineral acids, for example as halides, such as chlorides, as salts or organic acids, for example as acetates, or in the form of organic metal compounds, for example as cyanides or acetylacetonates. Suitable catalysts are, for example, copper-I oxide or copper-II oxide, copper-II chloride or zinc-II chloride, copper-I cyanide, mercury-II acetate or cadmium-II acetate or, in particular, copper-II acetylacetonate. About 0.1 to 10%, preferably about 1 to 2%, of catalyst are used, relative to the phosphono-isocyanoacetic acid ester employed.

The phosphono-isocyanoacetates of the formula IV which are obtainable as intermediate products and which were hitherto unknown are also a subject of the present invention. In preferred compounds of the formula IV, R and $R_1$ have the meanings indicated as preferred under formula I.

The process also comprises those embodiments according to which compounds obtained as intermediate products are used as starting materials and the remaining process steps are carried out with these, or according to which the process is discontinued at any stage. Starting materials can also be used in the form of derivatives or can be formed during the reaction.

The examples which follow illustrate the invention.

EXAMPLE 1

Diethylphosphono-isocyanoacetic acid tert.-butyl ester 1 ml of an approximately 2 molar solution of butyllithium in hexane is added over a period of 15 minutes to a solution, cooled to −10° C., of 282 mg (2 mmols) of isocyanoacetic acid tert.-butyl ester in 3 ml of dry hexane (distilled over sodium), whilst stirring vigorously and in a nitrogen atmosphere. The suspension which forms is stirred for a further 10 minutes and a solution of 413 μl (2 mmols) of diethyl phosphorochloridate in 5 ml of dry hexane is then added over a period of 15 minutes. The reaction mixture is stirred for a further 30 minutes, then treated with 20 ml of benzene and 5 ml of water and stirred vigorously for a further 10 minutes. The organic phase is washed with 3 times 5 ml of saturated aqueous sodium chloride solution, dried over sodium sulphate and evaporated in vacuo. The residue is chromatographed on silica gel. Benzene/ethyl acetate, 3:1, elutes diethylphosphono-isocyanoacetic acid tert.-butyl ester as a pale yellow oil; IR spectrum (in methylene chloride): characteristic bands at 3.4; 4.64; 5.70; 7.30; 8.00; 8.70 and 9.80μ.

The same compound can also be obtained as follows: (a) A solution of 530 mg (3.75 mmols) of isocyanoacetic acid tert.-butyl ester in 5 ml of tetrahydrofurane is added slowly, at −40° C., whilst stirring, to a mixture of 90 mg (3.75 ml) of sodium hydride in 5 ml of tetrahydrofurane and the mixture is stirred until the evolution of hydrogen has ceased. A solution of 774 μl (3.75 mmols) of diethyl phosphonochloridate in 5 ml of tetrahydrofurane is then added and the mixture is stirred for a further 30 minutes at the same temperature. After adding 1 ml of water, the mixture is diluted with 30 ml of methylene chloride and the organic phase is washed with water. The organic phase is dried over sodium sulphate and evaporated in vacuo. The residue is chromatographed on silica gel using toluene/ethyl acetate, 3:1, as the running agent and diethylphosphone-isocyanoacetic acid tert.-butyl ester with the abovementioned properties is obtained.

EXAMPLE 2

Thioformamido-diethylphosphonoacetic acid tert.-butyl ester

Dry hydrogen sulphide gas is passed for 10 minutes into a solution, cooled to 0° C., of 277 mg (1 mmol) of diethylphosphono-isocyanoacetic acid tert.-butyl ester in 5 ml of dry tetrahydrofurane (filtered through aluminium oxide). After adding a few crystals of copper-II acetylacetonate, the reaction vessel is closed and left to stand overnight at room temperature. The reaction mixture is filtered and the filtrate is evaporated in vacuo. The residue is chromatographed on silica gel thick layer plates with toluene/ethyl acetate, 1:1, and gives thioformamido-diethylphosphonoacetic acid tert.-butyl ester in the form of a colourless oil: IR spectrum (in methylene chloride): characteristic bands at 3.13; 3.35; 5.75; 7.01; 8.10; 8.70 and 9.75μ.

I claim:
1. A compound of the formula

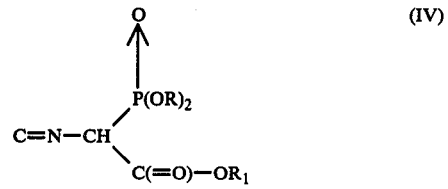

wherein R represents lower alkyl, aryl or aryl-lower alkyl and $R_1$ represents a radical which protects the carboxyl group.

2. A compound according to claim 1 which is diethylphosphono-isocyanoacetic acid tert.-butyl ester.

3. A compound according to claim 1, wherein R is lower alkyl with 1–4 carbon atoms, and wherein $R_1$ denotes a lower alkyl radical with 1 to 7 carbon atoms, halogenolower alkyl, wherein halogen has an atomic weight of more than 19, lower alkoxy-lower alkyl, lower alkylthio-lower alkyl, aryloxy-lower alkyl, aralkoxy-lower alkyl, arylcarbonylmethyl, polycycloaliphatyl, 1-oxa-cycloaliphat-2-yl, 1-thia-cycloaliphat-2-yl, wherein said cycloaliphat-2-yl group has from 5–7 ring atoms, or an aralkyl radical with 1 or 2 aryl radicals.

* * * * *